United States Patent [19]
Saussereau

[11] Patent Number: 4,779,858
[45] Date of Patent: Oct. 25, 1988

[54] IMMOBILIZING APPARATUS FOR PERFORMING MEDICAL AND PARAMEDICAL PROCEDURES

[75] Inventor: Guy Saussereau, Isère, France

[73] Assignee: Gerinnove, Isère, France

[21] Appl. No.: 1,587

[22] Filed: Jan. 9, 1987

[51] Int. Cl.⁴ .............................................. A61G 13/00
[52] U.S. Cl. .................................... 269/328; 378/209
[58] Field of Search ........................ 269/322, 323, 328; 378/208, 209

[56] References Cited
U.S. PATENT DOCUMENTS

| | | | |
|---|---|---|---|
| 3,449,570 | 6/1969 | Kok | 378/209 |
| 3,655,178 | 4/1972 | Vezina | 269/323 |
| 3,746,332 | 7/1973 | Hakistan | 269/328 |
| 3,933,154 | 1/1976 | Cabansag | 269/328 |
| 4,205,669 | 6/1980 | Hamann | 269/328 |
| 4,400,820 | 8/1983 | O'Dell et al. | 378/209 |
| 4,520,805 | 6/1985 | St Vincent et al. | 269/328 |

FOREIGN PATENT DOCUMENTS

| | | | |
|---|---|---|---|
| 1111847 | 3/1956 | France | 269/328 |
| 2587898 | 4/1987 | France | 378/209 |

Primary Examiner—Frederick R. Schmidt
Assistant Examiner—Judy J. Hartman
Attorney, Agent, or Firm—Herbert Dubno; Andrew M. Wilford

[57] ABSTRACT

An apparatus for immobilizing a patient so as to perform on this patient medical and paramedical procedures, in particular x-rays, this apparatus having a holding device that is upwardly open and set up to receive the patient (8) when laying down.

It has a rigid, preferably rectangular, oblong base (1) of a material permeable to x-rays, and has sides (3 and 4) that are closed and foldable against the patient, the sides being of a material permeable to x-rays and having the general shape of channels attached to the long edges of the base and of a convexity directed when they are against the patient toward the longitudinal axis of the base, tightening elements (5) permeable to x-rays being also provided to solidly maintain these channels in lateral contact with the patent.

19 Claims, 5 Drawing Sheets

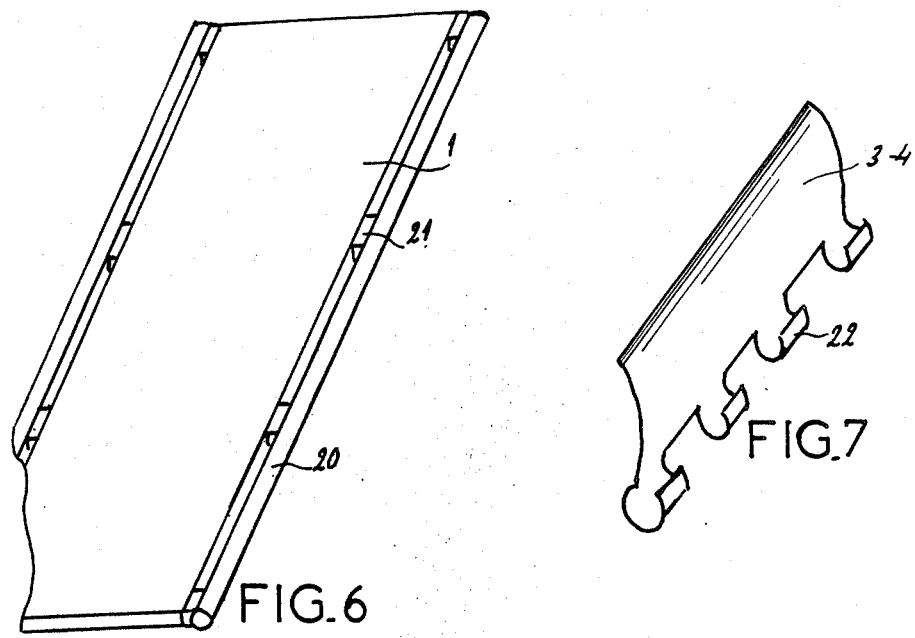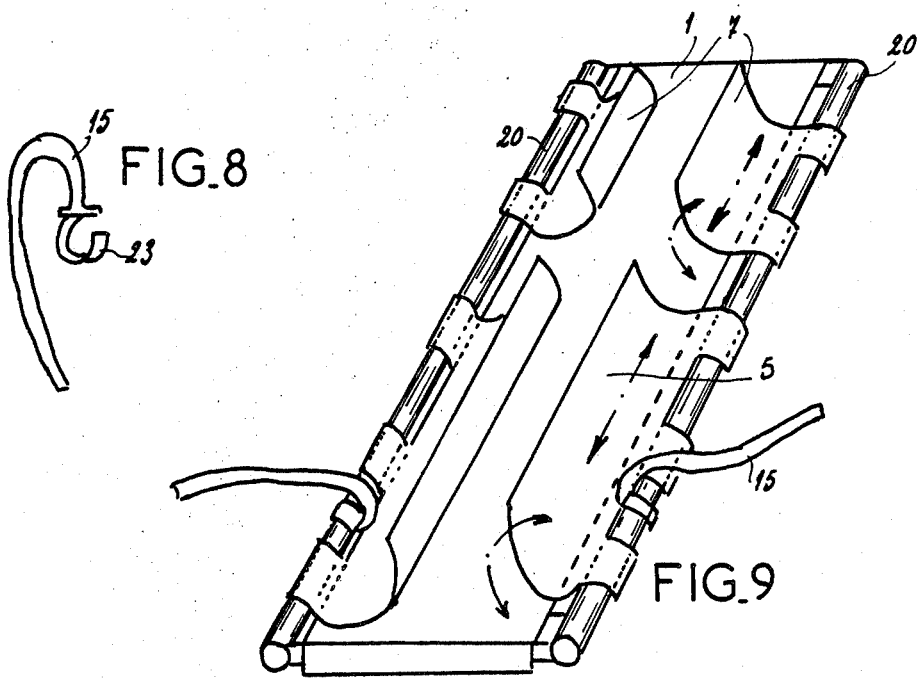

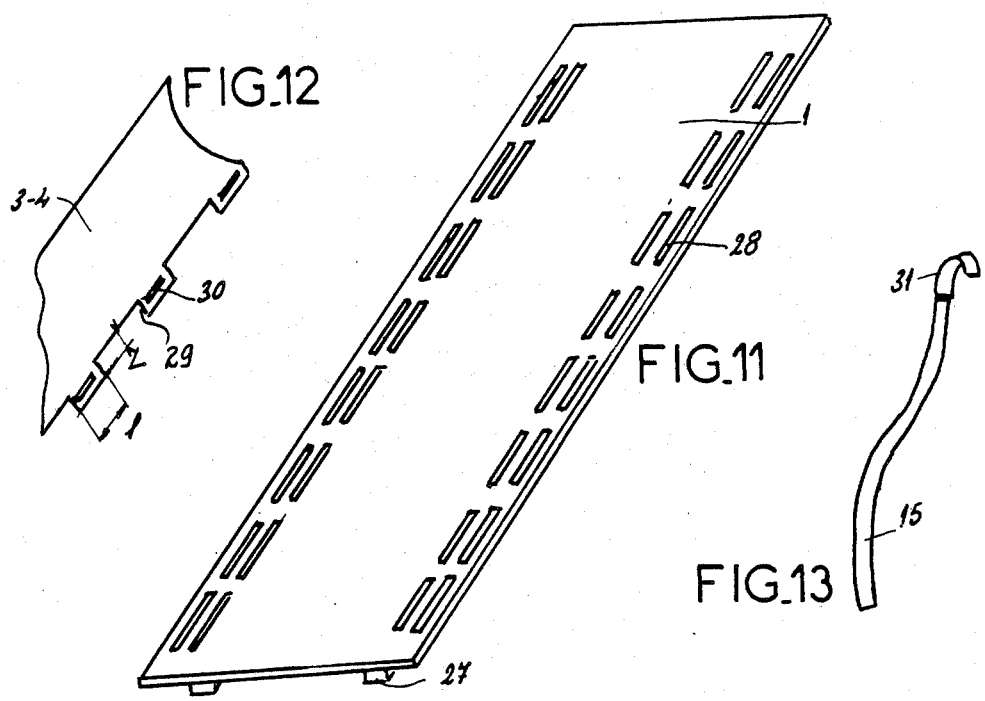
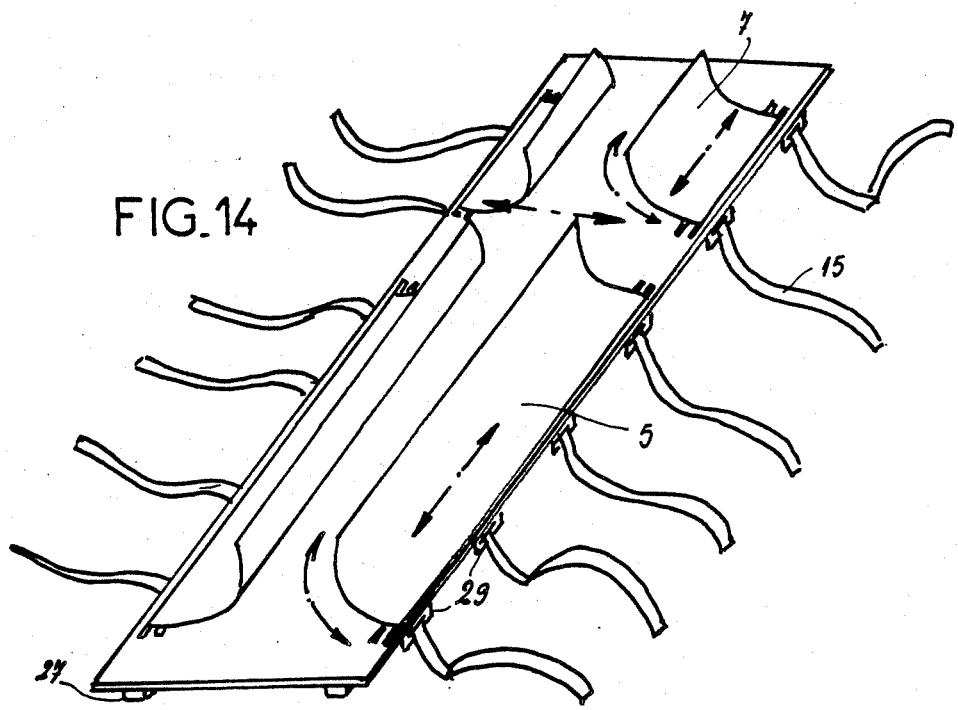

IMMOBILIZING APPARATUS FOR PERFORMING MEDICAL AND PARAMEDICAL PROCEDURES

FIELD OF THE INVENTION

The present invention relates to an apparatus for immoblizing a patient so as to perform on this patient medical and paramedical procedures, in particular an x-ray procedure.

BACKGROUND OF THE INVENTION

In order to take x-rays of an infant, a senile person, or an injured person it is generally indespensable to immobilize the patient. There are numerous immobilizing devices generally having a base that is flat or channel-shaped, the patient being held on this base by transverse straps or by a similar setup. U.S. Pat. Nos. 3,655,178 and 3,449,570 for example describe immobilizing devices of this type.

These known devices do not make it possible to efficiently hold very young children, up to three years old, and do not allow the taking of all types of x-rays without detaching the patient. They also are constructed for a person of a certain size—only for infants, only for children, or only for adults, for example—and are not universal. A large radiology laboratory must therefore stock several of these immobilizing devices, for example four to five.

As far as injured person are concerned, there are not at present containing devices whose sides are raisable against the ribs of the patient and which allow the patient to be tended to, immobilized along his full body length, the device allowing the injured person to be immobilized at the site, transported with the assistance of this device, and given any type of x-ray on arriving at the hospital without having to detach and manipulate him.

The immobilizing apparatus of the invention does not have the disadvantages of these known devices. It is intended for persons of all sizes and maintains the person efficiently on his face, back, or side. It allows one to perform on him all kinds of x-ray procedures in all positions and can also serve to immobilize an injured person at the site and to transport him without detaching him from it when he arrives as the hospital for first aid and in any case for x-rays. The immobilization is effected rapidly without pressing on the ventral area which is very advantageous in certain cases, and by simple and straightforward means. This apparatus is basically a holding device with an open top that can receive the patient while the patient lying down. It has a rigid, preferably rectangular, oblong base preferably of a material permeable to x-rays, and has sides that are closed and foldable against the patient. These sides are of a rigid or semirigid material permeable to x-rays and have the general shape of channels attached to the long edges of the base and whose convexity is directed when they are against the patient toward the longitudinal axis of the base, tightening elements permeable to x-rays, for example straps, being also provided to solidly maintain these channels in lateral contact with the patent. Preferably this apparatus is entirely made of nonmagnetic materials which allows the patent for example to be subjected to magnetic-resonance treatments.

The base is preferably flat and preferably of rectangular outline. It is advantageously provided with handles allowing the device to be used as a stretcher.

The device is advantageously fitted to receive fixing or hanging accessories to orient it in different positions, horizontal or vertical, in order to take various kinds of x-rays.

BRIEF DESCRIPTION OF THE DRAWING

The invention will be better understood as to its advantages and other characteristics from the following description of several embodiments, reference being made to the accompanying drawings in which:

FIGS. 6 to 9 respectively show the base, a side channel, a tightening strap, and the entire apparatus in another embodiment;

FIGS. 11 to 14 respectively show the base, a side channel, a tightening strap, and the entire apparatus in yet another embodiment;

SPECIFIC DESCRIPTION

Figure 1:
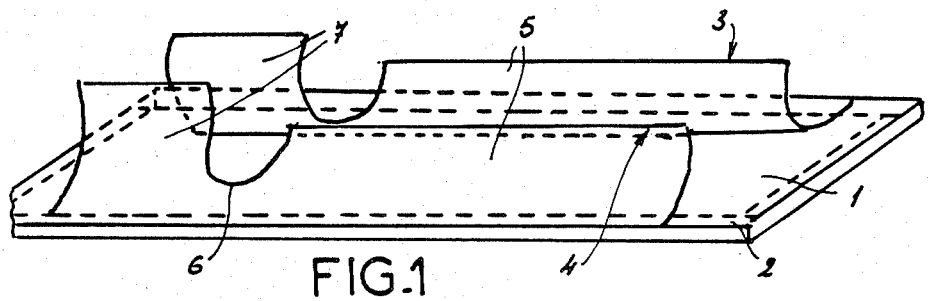
FIG. 1 is a perspective view of the apparatus in a stripped embodiment.

In the embodiment of FIG. 1 the immobilizing apparatus comprises a rigid base 1 reinforced by a frame 2 that is even more rigid, of rectangular shape and having long sides to which are soldered or glued the edges of two semirigid channels or side flaps 3 and 4 which extend tangentially to the upper surface of the base 1 and form the sides of the containing device. The convexity of the channels 3 and 4 is directed toward the longitudinal axis of the base 1 when the channels extend upwardly in a patient-receiving position of the device. The base 1, its frame 2, and the channels 3 and 4 are of a transparent plastic material that is mechanically strong, permeable to x-rays, and nonmagnetic. For example they can be made of polycarbonates.

Each side channel 3 and 4 is composed from the left to the right in the drawing of a first elongated part 5 serving to maintain the torso and the lower limbs, of a narrowed part 6 through which the arms can pass, and of an end part 7 that is much shorter and slightly wider than the part 5, serving to hold the head. The greatest dimension of the part 7 serves principally to avoid parasitic images.

In use the patient is laid on the base 1, the side walls or flaps 3 and 4 are closed against the ribs of the patient so that convex surfaces thereof contact the patient, and these walls are pressed against the patient by means of straps permeable to x-rays and not shown in this figure.

The semirigid side channels confine the patient laterally while pressing him lightly against the base.

Figure 2:
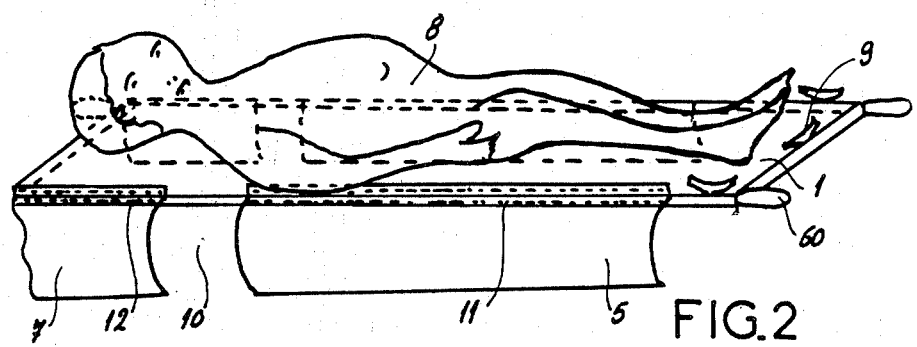
FIG. 2 is a perspective view of this apparatus, open on a patient in a slightly modified embodiment.

FIG. 2 shows a variant of this containing apparatus with a patient 8 laying on the base 1. The base 1 is provided with handles 60 which make it into a stretcher such that the containing apparatus can also serve for transporting the patient. Hooks 9 are provided along the short sides of the base to attach lines from arm or ankle bands. The parts 5 and 7 of the same channel, which are here separated by a space 10 to accommodate the arms, are pivoted on the longitudinal edges of the base by hinges 11 and 12 which are fixed half on the channels 5 and 7 and half on the base 1.

Figure 3:
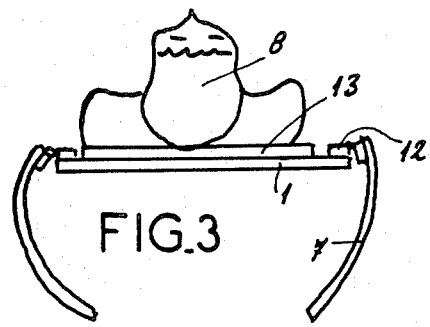
FIG. 3 is an end view of the apparatus of FIG. 2 with a mattress under the patient.

FIG. 3 shows that it is possible to put between the patient 8 and the base 1 a mattress 13 formed according to a feature of the invention of a plastic closed-cell foam. The inventor has discovered that this material has excellent mechanical and radiological qualities. This plastic foam is for example a polyurethane. The mattress 13 improves the comfort and allow one to avoid parasitic images.

Figure 4:
FIG. 4 is a view like that of FIG. 3 with the lateral channels up and cushions interposed between the channels and the head of the patient.

FIG. 4 shows that it is possible, when the side channels 7 are raised toward the head of the patient, to interpose also cushions 14 between these channels and the head. Preferably these cushions are also of a plastic closed-cell foam.

Figure 5:
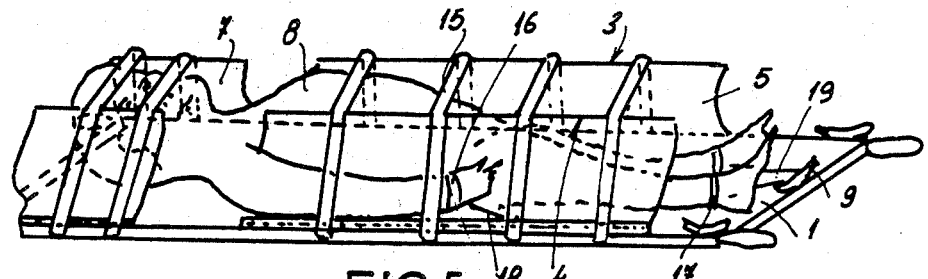
FIG. 5 is a perspective view of the same apparatus in the closed position holding the patient.

FIG. 5 shows the patient 8 immobilized thanks to the apparatus of FIG. 2. The assembly of the channels 7, 5 is folded onto the patient, these channels pressing not only laterally but also downward, at an angle toward the axis of the base without exercising any ventral or frontal pressures. Straps 13 of a nonmagnetic material permeable to x-rays go around the assembly and constitute, when they are tensioned and their ends are fixed to each other by a knot or the like, tightening elements which tend to pull the edges of the respective side channels toward each other from opposite sides of the base 1. Wrist bands 16 and ankle straps 17 fit around the wrists and ankles of the patient and laces 18 and 19 attach them to the hooks 9. The laces 18 and 19 are very tight so as to maintain the arms and legs of the patient in hyperextension.

Another embodiment of this containing apparatus, which has the advantage of being entirely and rapidly disassemblable, is shown in FIGS. 6 to 9.

According to this embodiment the base is bounded on its long sides by cylindrical bars 20 which are slightly spaced from the edges of the base by spacers 21 (FIG. 6). The channels 3 and 4 (FIG. 7) are all equipped on their sides hinged on the edges of the base of quick-connect attachments formed by open fixing rings 22 around the bars 20. These open rings 22 are of a convexity opposite to that of the channel 5, this channel 5 and each ring 22 having a common generatrix. Similarly the fixing straps 15 (FIG. 8) are also provided with open semirigid fixing rings 23 around the bars 20.

The completely assembled apparatus with the rings 22 and 23 snapped around the side bars is shown in FIG. 9. Preferably the spacers are positioned such relative to the open rings 22 that they allow some sliding of each channel 5 or 7 (FIG. 9) along the bar 20 on which it is pivoted; thus one can adjust the position of each channel along the longitudinal edge of the base 1.

The free ends of the straps 15 are fitted for example with self-attaching closures of the Velcro (registered mark) type as is also equally possible for the straps of the apparatus of FIG. 5.

Figure 10:
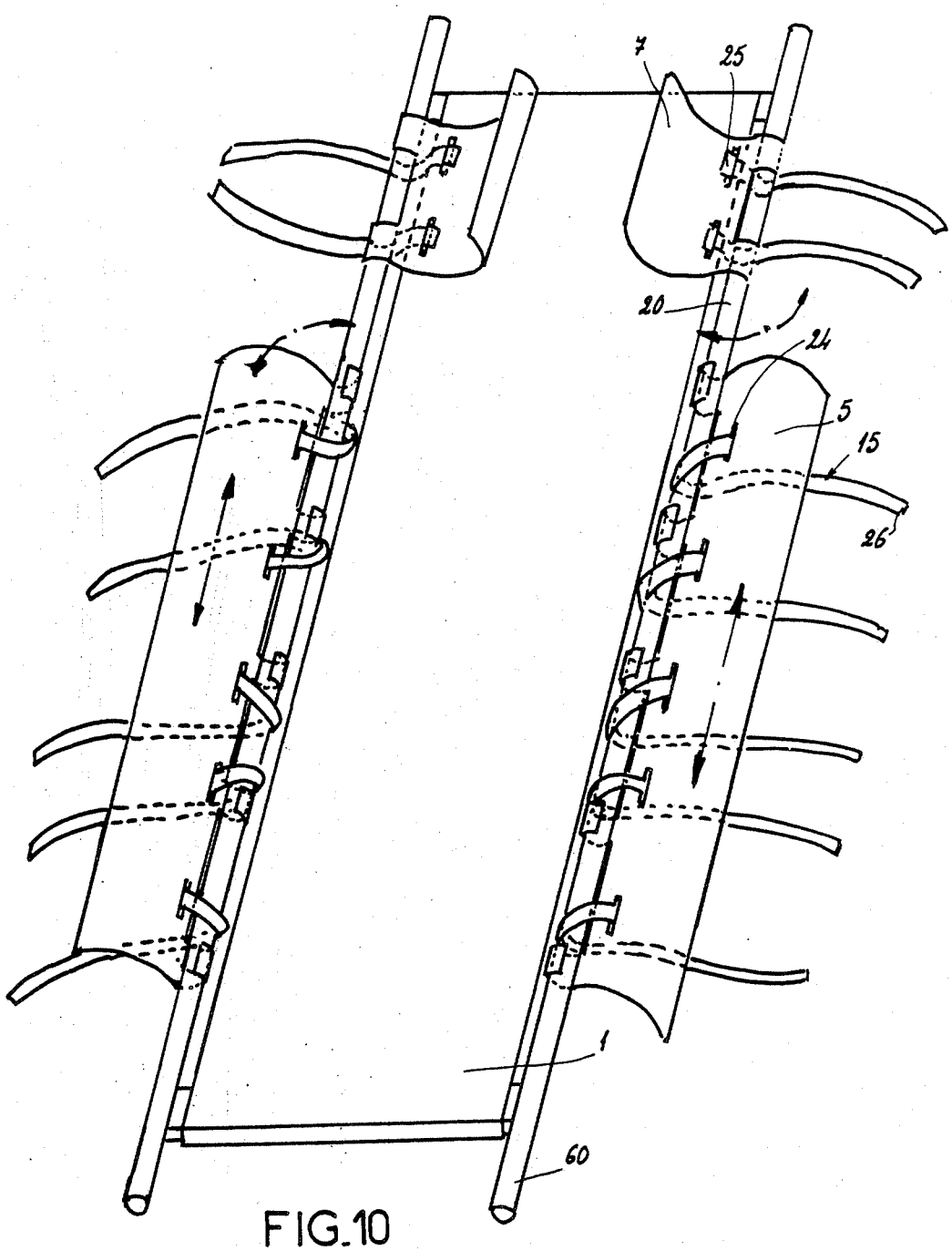
FIG. 10 is a variant on the embodiment of FIG. 9.

FIG. 10 shows a different embodiment of the apparatus of FIG. 9. This embodiment differs from the preceding one in that the cylindrical side bars project from 10 to 20cm at each of their ends so as to define four handles 60 allowing the base to be used as a stretcher. In addition the pivoted side channels 5 and 7 have rows of slots 24 near their edges each traversed by a strap 15. In this case the straps 15 do not have open rings but in their place they have at the end opposite to their free end an end stop 25 formed for example by a doubling of the fabric. The free end 26 is poked through each slot 24 from the concave side of the channel 5; then one slips it between the adjacent cylinder 20 and the base 1 to go around this cylinder and the concave face of the channel 5. Pulling the ends 26 over the base causes the channel 5 to pivot toward the patient and the assembly is tightened by attaching the ends 26 of the straps 15 to the ends of the corresponding straps located symmetrically on the other side of the base 1. This embodiment is advantageous to immobilize the patient because the straps 15 tend at the same time they pull on the lower part of each channel to move together this lower part to the sides of the patient and as they push the upper section of each channel toward the longitudinal axis of the base they exert on the patient pressure from top to bottom pushing him onto the base.

FIGS. 11 to 14 are similar to FIGS. 6 to 9 in yet another embodiment. The base 1 which is here reinforced by beams underneath the base is provided on each of its long sides with two rows of slots 28, these rows being parallel to the longitudinal axis of the base and parallel to one another.

The channels 3 and 4 are provided on the edge which is pivoted on the base 1 with tabs 29 of a width smaller than that of the slots 28, each tab 29 being also formed with a throughgoing slot 30 parallel to the longitudinal axis of the channel. The length L of each tab 29 is substantially greater than the thickness of the base 1 so that the tabs stick out with their slots 30 underneath same (see FIG. 14).

The straps 15 each have at one of their ends a hook 31 which lets them be fixed, after the channels are mounted by pushing the tabs 20 into one of the two rows of slots 28, in one of the slots 30. Another stop arrangement, such as a doubling of the fabric, can be used in place of the hook 31.

Assembly takes place as follows (FIG. 14):

According to the size of the patient the tabs 29 of the channels 5 and 7 are fitted into one or the other of the two parallel rows of slots 28: for a skinny patient they are put into the row closer to the longitudinal axis and for a bigger patient they are put into the row closer to the outer edge of the base 1. The axial positions of the channels 5 and 7 are then adjusted by moving them longitudinally in the slots 28. Immobilization is then carried out by hooking the straps 15 into the slots 30 and by stretching them over the patient so they can be secured at the end to the respective straps as above.

Figure 15:
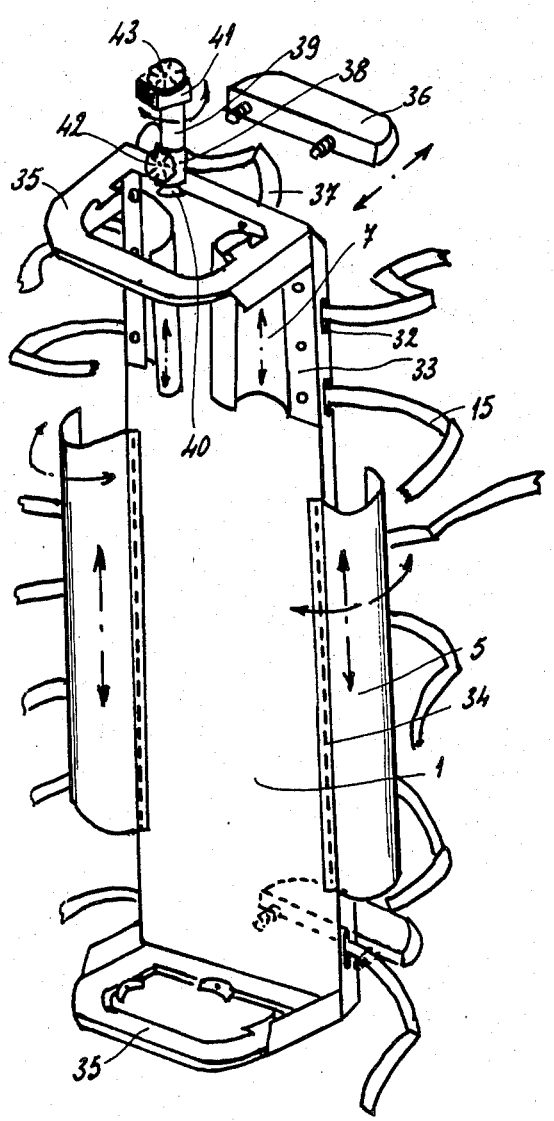
FIG. 15 is a perspective view of an immobilizing apparatus according to the invention equipped with fittings for positioning and hanging it.

According to another feature of the invention the containing apparatus is set up to receive fittings serving to position it virtually any way in order to be able to carry out various x-ray procedures on the patient. FIG. 15 shows a containing apparatus incidentally in another embodiment which is provided with such positioning fittings.

In the embodiment of FIG. 15 the straps 15 are fitted into the side slots formed at the edge of the long sides of the frame 1 or in its reinforcing frame. They go around the base or are fixed as described above (cf. FIG. 10) at their ends at the opening of the slots 32 by a stop or a doubling of the fabric. In addition all the side channels are adjustable longitudinally by sliding in tracks parallel to the longitudinal axis of the base; in this example the side channels 7 that hold the head are longitudinaly slidable and are compressed between plates 33 and the base, while the channels 5 that hold the torso and legs are fixed on hinges that themselves slide longitudinally in the tracks which are not shown but are similar to the tracks 33.

Screwed or welded to the short sides of the base 1 are two positioning frames 35. The frames 35 are perpendicular to the base 1 and are located on the side which normally receives the patient. They have the shape of a rectangle with rounded upper corners. They can be otherwise shaped, for example semicircular. They are each extended at opposite sides of the base by a fixed piece 36 of substantially the same shape but shorter relative to the surface of the base 1.

Underneath the base 1 at its end receiving the head of the patient a metallic plate 37 is fixed on which is welded a hollow tube 38, for example of steel, having an axis parallel to that of the base 1. A tubular shaft 39 can rotate in the cylindrical hollow tube 38, fixed at its lower end by a collar 40 and having at its upper portion a piece of rectangular-section tube 41 having an axis perpendicular to that of the tube 39. The hollow tubes 38 and 41 are traversed by locking screws 42 and 43. The tube 41 serves to receive a square or rectangular peg serving to suspend or fix it.

Figure 16:
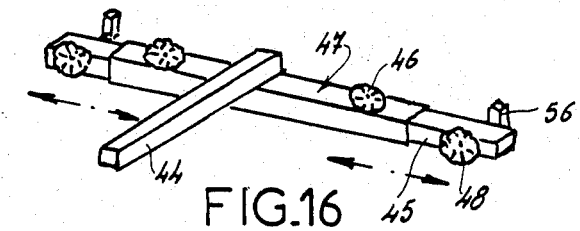
FIG. 16 is a hanging support for the assembly of FIG. 15 for attachment to an x-ray table.

FIG. 16 shows an example of a a device for securing the assembly of FIG. 15 to an x-ray table. It is formed of a peg 44 of rectangular section that can fit snugly in the little tube 41 and that is welded crosswise on a fixing bar 47 that an telescope thanks to sliding elements 45 that can be fixed at the desired length by screws 46. The bar 47 can be fixed by attachments 56 on a frame element of the radiology table, screws 48 serving to secure it in position on this frame element.

This positioning device allows the patent to be sat in any position: from the front or side, obliquely, standing up, recumbent, on the front or on the back. The patient is positioned by turning the base 1 about the axis of the cylinder 39.

Figure 17:
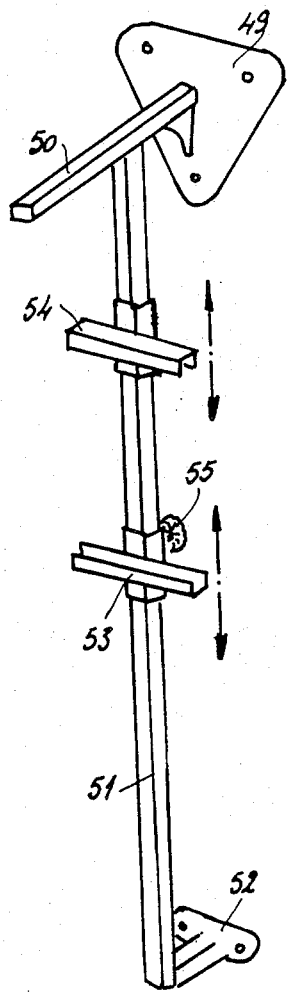
FIG. 17 shows a hanging support for the same assembly for attachment to a wall.

FIG. 17 shows a device replacing that of FIG. 16 in the situation where there is no x-ray table. It has an upper plate 49 for fixation for example on the wall, a horizontal rectangular bar 50 forming the crosspiece taking the place of the bar 44 of FIG. 16, and a main bar 51 slidably supporting two horizontal jaws 53 and 54 for holding x-ray films as is known. The lower jaw 53 can be locked in position on the bar 51 by means of a screw 55.

The invention is not limited to the embodiments that have just been described and numerous variations are imagined. The curvature of the side channels can be irregular; they can be formed by groups of curves or of flat segments all connected together. The side channels can be rigid instead of semirigid as is preferable; in this case one would put cushions between the channels and the patient. The way of fixing the side channels on the base can be other than those described: molding, riveting, screwing. The invention is not limited to use with humans and can advantageously be applied to the veterinary field. One single model of this immobilizing apparatus set up for four-legged animals can be used in a veterinary clinic for x-ray or magnetic-resonance work on cats or dogs of small or medium sizes. Certain of the hinges or other strong elements of this type can be of metal if they are located in places that would be no hindrance to radiological work. The straps can have buckles. The base, although preferably flat, can in certain cases be slightly arced with the convexity or concavity toward the patient. The base need not be rectangular. The channels can be used only for holding a portion of the body of the patient, for example the head, etc.

I claim:

1. An apparatus for immobilizing a patient so as to perform on this patient medical and paramedical procedures including a procedure, in particular in which the patient is subjected to x-rays on the apparatus while immobilized, said apparatus comprising:
   a rigid, generally elongated base of a material permeable to x-rays and having opposite longitudinal edges, said base being of a length sufficient to receive the head, trunk and legs of the patient;
   elongated side flaps extending continuously over major parts of the length of the base and disposed along respective ones of said opposite longitudinal edges and foldable against the patient at least along the trunk and legs thereof, said side flaps each being of a material permeable to x-rays and having the general shape of a channel, each of said side flaps having a transverse curvature such that it is convex inwardly toward the patient;
   means attaching each side flap at an edge thereof to a respective longitudinal edge of the base so that convex surfaces of said side flaps are against the patient and turned inwardly toward a longitudinal axis of the base to flank the patient; and
   tightening elements supported by the base permeable to x-rays for solidly maintaining said side flaps with said convex surfaces in lateral contact with the patient over the trunk and legs thereof.

2. The immobilizing apparatus of claim 1 wherein said base, said side flaps said elements are all made of nonmagnetic materials.

3. The immobilizing apparatus according to claim 1, characterized in that said side flaps are of a semirigid material.

4. The apparatus according to claim 3 wherein said side flaps are fixed on the longitudinal edges of the base tangentially to an upper surface thereof.

5. The apparatus according to claim 1 wherein said side flaps are hinged on the edges of the base.

6. The apparatus according to claim 5, further comprising means for adjusting a longitudinal position of said side flaps.

7. The apparatus according to claim 1, wherein said base is provided with handles to form a stretcher.

8. The apparatus according to claim 1, wherein said base is flat.

9. The apparatus according to claim 1, wherein said base is of rectangular shape.

10. The apparatus according to claim 1, wherein said base is reinforced by a frame.

11. The apparatus according to claim 1, wherein said base is reinforced by longitudinal beams.

12. The apparatus according to claim 1 wherein each of said sides flaps is formed of at least two channels separated by a space, one of the channels of each side slap being intended to hold the head of the patient.

13. The apparatus according to claim 12 wherein the channels for holding the head of the patient extend above a patient receiving surface of the base when the base is horizontal to a greater extent than the other channels of the respective side.

14. The apparatus according to claim 1, further comprising a mattress below the patient and cushions between the side flaps and the head of the patient, said mattress and cushions being of a closed-cell plastic foam.

15. The apparatus according to claim 12 wherein said side flaps are constructed and arranged to be removed and fixed to the longitudinal edges of the base by fast-acting attachments.

16. The apparatus according to caim 15, further comprising means for changing spacing of the side flaps from the longitudinal axis of the base.

17. The apparatus according to claim 1 wherein said side flaps are provided with slots for straps, said slots being located near edges of the side flaps attached to the base, said traps being fitted such that tightening them causes when a patient is immobilized a traction on lower parts of said side flaps in the direction of the patient.

18. The apparatus according to claim 1, where said side flaps are constricted only to hold one part of the body of the patient.

19. The apparatus according to claim 1, wherein said base has fittings (37) for fixing it in different positions.

* * * * *